United States Patent [19]

Drake

[11] Patent Number: 4,487,970
[45] Date of Patent: Dec. 11, 1984

[54] CLEAVAGE OF HYDROPEROXIDES

[75] Inventor: Charles A. Drake, Bartlesville, Okla.

[73] Assignee: Phillips Petroleum Company, Bartlesville, Okla.

[21] Appl. No.: 500,679

[22] Filed: Jun. 3, 1983

[51] Int. Cl.$^3$ ............................................. C07C 45/53
[52] U.S. Cl. ................................... 568/342; 568/311; 568/385; 568/798
[58] Field of Search ............... 568/385, 342, 798, 835, 568/342, 311

[56] References Cited

U.S. PATENT DOCUMENTS

| | | |
|---|---|---|
| 2,628,983 | 2/1953 | Aller et al. . |
| 2,628,984 | 2/1953 | Aller et al. . |
| 2,951,870 | 9/1960 | Cooke . |
| 3,497,561 | 2/1970 | Gelbein . |
| 3,925,495 | 12/1975 | Rodewald ............................ 585/331 |
| 3,959,381 | 5/1976 | Arkell et al. . |
| 4,116,880 | 9/1978 | Olah . |
| 4,267,380 | 5/1981 | Austin et al. ......................... 568/798 |
| 4,339,613 | 7/1982 | Olah .................................... 568/798 |

OTHER PUBLICATIONS

Rodewald, Chem. Abst., vol. 84, #124301c, (1976).

*Primary Examiner*—James H. Reamer

[57] ABSTRACT

Secondary-alkyl substituted benzene hydroperoxides are cleaved to form phenols and ketones by contacting the secondary-alkyl substituted benzene hydroperoxide with a catalyst consisting essentially of about 3:1 to 1:10 by weight of SbF$_5$ and graphite in the presence of an aromatic or ketone solvent at a temperature of from about 0°–100° C.

11 Claims, No Drawings

CLEAVAGE OF HYDROPEROXIDES

This invention relates to the cleavage of secondary-alkyl substituted benzene hydroperoxides to form phenols and ketones.

The use of aqueous acid catalyst systems such as $H_2SO_4$ and water for the cleavage of hydroperoxides to phenols and ketones is well known in the art. While such catalyst systems are operable for their intended use, they are not without disadvantages.

An aqueous acid catalyst system tends to make product separation (i.e. phenols and ketones) difficult because a neutralization step is frequently required. Furthermore, the use of aqueous acid systems sometimes results in the formation of azeotropes such that the products cannot be separated by either simple or fractional distillation. Therefore, a catalyst system which gives good yields and selectivities to phenols and ketones from the cleavage of hydroperoxides but avoids the problems mentioned above is highly desirable.

It is therefore an object of this invention to provide an improved process for the cleavage of hydroperoxides to phenols and ketones.

Other aspects, objects, and advantages of the present invention are apparent from the specification and claims.

In accordance with the present invention, I have discovered that secondary-alkyl substituted benzene hydroperoxides are effectively cleaved by contacting the hydroperoxide with a catalyst consisting essentially of a mixture of $SbF_5$ and graphite in the presence of an aromatic or ketone solvent. By utilizing such a catalyst system, relatively short reaction times, moderate reaction temperatures, and easy product-catalyst separation are accomplished.

The secondary-alkyl substituted benzene hydroperoxides contemplated for use in the present invention are represented by the general formulae:

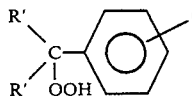     or     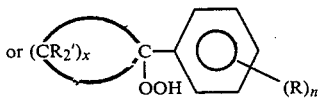

(I)                           (II)

wherein R is a $C_1$–$C_{20}$ alkyl, cycloalkyl, or alkaryl radical, R' is independently a $C_1$ to $C_{10}$ alkyl, aryl, or alkaryl radical, n is an integer from 0–5, and x is an integer from 2 to 11. Exemplary compounds falling under formula (I) suitable for use in the present invention include cyclohexylbenzene hydroperoxide, cumene hydroperoxide, sec-butylbenzene hydroperoxide, sec-pentylbenzene hydroperoxide, and sec-hexylbenzene hydroperoxide with cyclohexylbenzene hydroperoxide being preferred.

The catalyst employed in the present invention consists essentially of a mixture of $SbF_5$ and graphite. Generally the mixture of $SbF_5$ and graphite will be in the range of about 3:1 to 1:10 by weight, preferably about 2:1 to 1:2 and most preferably about 1:1. Typically about 0.01–10 weight percent, preferably about 0.1–3 weight percent of the catalyst is employed in the process based upon the weight of the hydroperoxide to be cleaved.

The graphite employed in the present invention may be any which is commercially available. Typically, the graphite will have a surface area of at least 5 $m_2/g$.

The $SbF_5$-graphite catalyst is typically prepared by placing the graphite in an inert atmosphere, such as $N_2$, and then dripping the $SbF_5$ onto the graphite with agitation to ensure uniform distribution of the $SbF_5$ on the graphite.

The catalyst is commercially available, for example, from Alfa Products, Thiokol/Ventron Division, Danvers, Mass.

The solvents utilized in the present invention include aromatics and ketone solvents.

Aromatic solvents contemplated for use in the present invention are represented by the following general formula:

(III)

wherein R" is a $C_1$ to $C_8$ hydrocarbyl radical and m is an integer from 0–6. Examples of such aromatics include benzene, toluene, m-xylene, p-xylene, and isopropyl benzene.

Ketone solvents useful in the present invention contain from 3 to 10 carbon atoms. Examples include acetone, methyl ethyl ketone, methyl isobutyl ketone and mixtures thereof.

In the present invention the compounds of formula (I) are cleaved to phenols and ketones. Examples include the cleavage of cyclohexylbenzene to phenol and cyclohexanone.

The process of the present invention is carried out by contacting the secondary-alkyl substituted benzene hydroperoxide with the $SbF_5$/graphite catalyst described above in the presence of a suitable solvent at a temperature in the range of from about 0°–100° C., with 10°–40° C. preferred.

The cleavage process can be carried out either batchwise or continuously, using a fixed catalyst bed, stirred batch reactor, a fluidized catalyst chamber, or other suitable contacting techniques.

Generally, the reaction time for batch reaction will be from about 1 min. to 5 hrs., preferably from about 5 to 60 minutes.

Generally, the LHSV for batch reaction will be from 0.1–10 with 0.2–4 preferred.

While the pressure at which the process of the present invention is carried out is not thought to be critical, it can be from about sub-atmospheric to 1000 psig with about atmospheric to about 100 psig preferred.

The reaction products may be isolated by conventional procedures such as distillation and extraction. The residual products, can, if desired, be purified by conventional procedures such as column chromatography or fractional recrystallization.

The following examples illustrate the present invention.

EXAMPLE I

Preparation of Cyclohexylbenzene Hydroperoxide

The cyclohexylbenzene hydroperoxide (CHBHP) feed employed in the following cleavage reaction was pooled from numerous laboratory investigations on the oxidation of cyclohexylbenzene (CHB), such as the following exemplary preparations. The pooled feed had a CHBHP concentration of 8.7 wt % in unreacted cyclohexylbenzene.

(a) Atmospheric oxidation of CHB:

A 300 mL 3-neck round bottom flask equipped with a dispersion tube and a magnetic stirrer was charged with 199 g of CHB and 1 g of cumene hydroperoxide. The flask was heated to 130° C. and $O_2$ introduced via the dispersion tube at about 0.8 SCFH. Reaction was carried out for four hours at 130° C. and atmospheric pressure, then reactor contents sampled and analyzed by gas liquid chromatography (glc) using an internal standard. Typical CHB conversions of about 28% with selectivity to CHBHP of about 70% were obtained.

(b) CHB oxidation under pressure:

A 300 mL stainless steel Autoclave Engineers Magnedrive stirred tank reactor was charged with 49 g of cyclohexylbenzene and 1 g of cumene hydroperoxide. The reactor was then sealed, pressurized with $O_2$ to about 180 psig, and heated to about 120° C. for four hours. Typical CHB conversions of about 17% with selectivity to CHBHP of about 74% were obtained.

This example describes the typical preparations of the cyclohexylbenzene hydroperoxide employed in the following cleavage runs.

EXAMPLE II

Catalyst Preparation

The catalysts employed for cleavage of cyclohexylbenzene hydroperoxide were prepared as follows.

Comparative Catalyst A was prepared by wetting 9 g of finely powdered acidic clay called Filtrol 24, marketed by Filtrol Corporation, with 1 g of $SbF_5$ under an inert ($N_2$) atmosphere.

Comparative Catalyst B was prepared by wetting 2.5 g of 50–200 mesh charcoal with 2.5 g of $SbF_5$ in an inert ($N_2$) atmosphere.

Inventive Catalyst C employed was a 1:1 mixture of $SbF_5$ and graphite available commercially under the brand Graphimet $SbF_5$—50 (Catalogue #81923) from Alfa Products.

EXAMPLE III

All cyclohexylbenzene hydroperoxide cleavage reactions were carried out in a 100 mL round bottom flask equipped with a magnetic stir bar. Generally, about 14 g of crude oxidation product (see Example I), 0.4 g of internal standard (n-pentylbenzene), 0.1–3.0 g of catalyst and about 10 mL of solvent were charged to the vessel. The reactor contents were stirred at room temperature for 30 minutes to about 2 hours, then sampled for analysis by gas liquid chromatography (glc). The product yields are corrected for the fact that only 90% of the hydroperoxide in the CHBHP feed is the correct hydroperoxide, i.e.

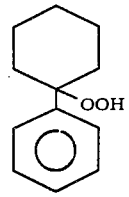

Other isomeric hydroperoxides are incapable of cleavage to give the desired ultimate products, phenol and cyclohexanone.

EXAMPLE IV

CHBHP Cleavage

Several cleavage reactions were carried out employing the catalysts described in Example II according to the general procedure set forth in Example III. Amount of catalyst used, solvents employed, reaction time and product analyses are summarized in the Table.

TABLE

| Run | Catalyst, g | CHBHP Chgd, g | Solvent, mL | Reaction Time min | Yield Phenol | Cyclohexanone |
|---|---|---|---|---|---|---|
| 1 | A, 3.0 | 4.8 | Acetone, 19 | 60 | 11.5 | 12.2 |
|   |       |     |             | 120 | 20 | 20 |
| 2 | B, 3.0 | 14.4 | Acetone, 9.5 | 60 | 89 | 81 |
|   |       |     |             | 120 | 89 | 79 |
| 3 | C, 0.2 | 14.2 | Acetone, 10 | 60 | 99 | 99 |
| 4 | C, 0.2 | 14.2 | Acetone, 10 | 30 | 99 | 99 |
|   |       |     |             | 60 | 97 | 99 |
| 5 | C, 0.1 | 14.2 | Benzene, 10 | 60 | 92 | 92 |
|   |       |     |             | 120 | 96 | 97 |
| 6 | C, 0.1 | 14.2 | Acetone, 10 | 60 | 98 | 99 |
|   |       |     |             | 120 | 91 | 93 |

The results of these experiments demonstrate that a mixture of $SbF_5$ and graphite (Runs 3–6) is a very active and selective catalyst for cleavage of cyclohexylbenzene hydroperoxide to give phenol and cyclohexanone.

Reasonable variations and modifications are possible from the foregoing disclosure without departing from the spirit and scope of the present invention.

I claim:

1. An improved process for the cleavage of a secondary-alkyl substituted benzene hydroperoxide of the formula:

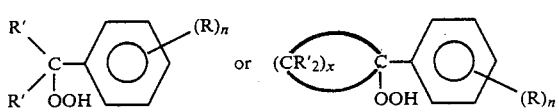

wherein R is a $C_1$–$C_{20}$ alkyl, cycloalkyl, or alkaryl radical, R' is independently a $C_1$ to $C_{10}$ alkyl, aryl, or alkaryl radical, n is an integer from 0–5, and x is an integer from 2 to 11, comprising contacting said hydroperoxide with a catalyst consisting essentially of about 3:1 to 1:10 by weight of $SbF_5$ and graphite in the presence of a solvent selected from the group consisting of (a) an aromatic hydrocarbon of the formula

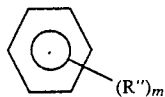

wherein R" is a $C_1$ to $C_8$ hydrocarbyl radical and m is an integer from 0-6; or (b) a $C_1$ to $C_{10}$ ketone;

at a temperature of from about 0°–100° C.

2. A process according to claim 1 wherein said secondary-alkyl substituted benzene hydroperoxide is cyclohexylbenzene hydroperoxide.

3. A process according to claim 1 wherein said solvent is acetone.

4. A process according to claim 1 wherein said solvent is benzene.

5. A process according to claim 1 wherein said temperature is from about 10° C. to about 40° C.

6. A process according to claim 1 wherein said $SbF_5$ and graphite are present in an amount of about 2:1 to 1:2 by weight.

7. A process according to claim 1 wherein said $SbF_5$ and graphite are present in an amount of about 2:1 to 1:2 by weight.

8. A process according to claim 1 wherein said catalyst is employed in an amount of from about 0.01 to 10 weight percent of said secondary-alkyl substituted benzene hydroperoxide.

9. A process according to claim 1 wherein said catalyst is employed in an amount of from about 0.1 to 3 weight percent of said secondary-alkyl substituted benzene hydroperoxide.

10. A process according to claim 1 wherein said secondary-alkyl substituted benzene hydroperoxide is cyclohexyl benzene and said solvent is acetone.

11. A process according to claim 1 wherein said secondary-alkyl substituted benzene hydroperoxide is cyclohexyl benzene and said solvent is benzene.

* * * * *